US006847899B2

(12) United States Patent
Allgeyer

(10) Patent No.: US 6,847,899 B2
(45) Date of Patent: Jan. 25, 2005

(54) DEVICE AND METHOD FOR QUALITATIVE AND QUANTITATIVE DETERMINATION OF INTRAVENOUS FLUID COMPONENTS

(75) Inventor: Dean O. Allgeyer, Los Angeles, CA (US)

(73) Assignee: Dean Allgeyer, M.D., Inc., Los Angeles, CA (US)

(*) Notice: Subject to any disclaimer, the term of this patent is extended or adjusted under 35 U.S.C. 154(b) by 76 days.

(21) Appl. No.: 10/264,666

(22) Filed: Oct. 4, 2002

(65) Prior Publication Data

US 2003/0204330 A1 Oct. 30, 2003

Related U.S. Application Data

(63) Continuation-in-part of application No. 60/375,691, filed on Apr. 26, 2002.

(51) Int. Cl.[7] .................................................. G06F 3/02
(52) U.S. Cl. .......................... 702/32; 702/31; 702/50; 702/188
(58) Field of Search .......................... 702/32, 38, 50, 702/75, 76, 115, 183; 356/301, 432, 436, 440; 600/532, 538; 128/92, 95

(56) References Cited

U.S. PATENT DOCUMENTS

| 4,109,647 A | * | 8/1978 | Stern et al. ................ 600/479 |
| 4,286,327 A | | 8/1981 | Rosenthal et al. .......... 364/498 |
| 4,620,284 A | | 10/1986 | Schnell et al. .............. 364/498 |
| 4,621,643 A | | 11/1986 | New, Jr. et al. ............ 128/633 |
| 5,226,886 A | | 7/1993 | Skakoon et al. ............ 604/153 |
| 5,239,860 A | | 8/1993 | Harris et al. ............... 73/61.48 |
| 5,406,084 A | | 4/1995 | Tobler et al. ........... 250/339.01 |
| 5,750,998 A | | 5/1998 | Goldman ................... 250/343 |
| 5,879,294 A | | 3/1999 | Anderson et al. .......... 600/310 |
| 5,995,858 A | | 11/1999 | Kinast ....................... 600/323 |
| 6,070,761 A | | 6/2000 | Bloom et al. ................ 222/81 |
| 6,072,576 A | | 6/2000 | McDonald et al. ......... 356/300 |
| 6,111,639 A | | 8/2000 | Reduto ....................... 356/300 |
| 6,122,042 A | | 9/2000 | Wunderman et al. ........ 356/73 |

(List continued on next page.)

FOREIGN PATENT DOCUMENTS

| WO | WO 98/19592 A1 | 5/1998 | ............ A61B/5/00 |
| WO | WO 98/56028 A1 | 12/1998 | ............ H01J/49/04 |
| WO | WO 99/62574 A1 | 12/1999 | ............ A61M/1/16 |

OTHER PUBLICATIONS

Joint Commission on Accreditation of Healthcare Orgs; *Sentinel Event Alert*, vol. 11. Nov. 1999.
J. Phillips, et al., *Retrospective Analysis Of Mortalities Associated With Medication Errors*, Am.J. Health–Syst. Pharm., vol. 581, Oct. 2001.
*Alaris Medical Systems Solutions*, vol. 6, Winter 2001.
*U.S. Food and Drug Administration Performance Plan*, 1.2.1 Strategies, 2002.
B. Braun Horizon Outlook™, *IV Safety Infusion System Is First To Address Proposed FDA Bar Code Requirements*, Sep., 2002.
*Care Suite Interfaces To Infusion Pumps To Reduce Medical Errors & Improve Patient Safety Efforts*, www.picis.com/hmtl/news/article, Oct. 2, 2002.

*Primary Examiner*—Patrick Assouad
*Assistant Examiner*—Felix Suarez

(57) ABSTRACT

A device and process for preventing medical errors due to the improper administration of an intravenously delivered medication includes the spectroscopic analysis of intravenous fluid components. An emission source and detector are placed adjacent to the intravenous tubing of an administration set to generate signals for spectroscopic analysis. The signals are processed to identify the medication and, in certain embodiments of the invention, can determine the medication's concentration. In a preferred embodiment, the emission source, detector, and hardware and software for the spectroscopic analysis are placed in an infusion pump.

50 Claims, 8 Drawing Sheets

U.S. PATENT DOCUMENTS

| | | |
|---|---|---|
| 6,122,536 A | 9/2000 | Sun et al. .................... 600/341 |
| 6,236,041 B1 | 5/2001 | Donnerhack et al. ........ 250/281 |
| 6,236,048 B1 | 5/2001 | Ditmarsen et al. ...... 250/339.12 |
| 6,261,262 B1 | 7/2001 | Briggs et al. ................ 604/153 |
| 6,271,521 B1 | 8/2001 | Saathoff et al. ......... 250/339.04 |
| 6,278,889 B1 | 8/2001 | Robinson .................... 600/322 |
| 6,362,891 B1 | 3/2002 | Axon et al. .................. 356/433 |
| 6,629,934 B2 * | 10/2003 | Mault et al. ................. 600/538 |
| 2003/0139681 A1 * | 7/2003 | Melker et al. .............. 600/532 |

\* cited by examiner

DEVICE AND METHOD FOR QUALITATIVE AND QUANTITATIVE DETERMINATION OF INTRAVENOUS FLUID COMPONENTS

This application is a continuation-in-part of provisional application Ser. No. 60/375,691, filed Apr. 26, 2002.

FIELD OF THE INVENTION

This invention relates generally to devices and methods of preventing medication errors. Specifically, utilization of spectroscopy for the qualitative and quantitative determination of fluid path components is disclosed. Spectroscopy can be applied to intravenous infusions where the determination of fluid path components can significantly decrease and prevent the occurrence of medication errors.

BACKGROUND OF THE INVENTION

Medical errors are recognized as a serious problem associated with the delivery of health care. The Institute of Medicine estimates that as many as 98,000 Americans die annually as a result of preventable medical errors. Medication errors constitute a critical component of medical errors in general. The Joint Commission on Accreditation of Healthcare Organizations (JCAHO) stated in the Nov. 19, 1999 *Sentinel Event Alert*, "Medication errors are one of the most common causes of avoidable harm to patients in health care organizations." The 2001 publication "Retrospective Analysis of Mortalities Associated With Medication Errors," *Am. J. Health-Syst. Pharm.*, Vol. 58, Oct. 1, 2001, reported that among fatal medication errors, improper dose (40.9%) and administering the wrong drug (16%) were the most frequent. The FDA 2002 Performance Plan proposes the development of standards to prevent dosing and drug mix-ups.

Medication errors are attributable to one or more of fourteen causes that span the range from conceiving a therapeutic regimen to the delivery of a pharmaceutical compound. The top six mistakes, according to the *Am. J. Heath-Syst. Pharm.* article, constitute 80 per cent of all medication errors and are, in decreasing frequency, wrong dose, wrong drug, wrong route of administration, wrong patient, wrong rate, and wrong concentration. A number of commercially available products attempt to address the need to decrease the incidence of medication errors and are directed at various aspects of the possible mistakes. These products utilize software, drug libraries, and institutional limits placed on specific drugs.

For example, Alaris Corporation markets a software system named Guardrails™. Guardrails™ provides protection against infusion programming errors with tests of reasonableness during the initial programming and in subsequent programming of intravenous (IV) infusions. The system includes pre-programmed drug maximums that cannot be overridden by faulty bedside data input. The system, however, still leaves the potential for wrong drug, wrong patient, wrong rate, and wrong concentration errors.

Picis Corporation also offers medication management and data collection software trademarked as CareSuite™. An excerpt from its literature states: "Simply obtaining the infusion dose or rate from the intravenous pump would not be enough without automatically identifying the drug being administered. Thus the goal was to minimize computation and recording errors and give clinicians greater control over fluid management. With automatic data collection by Care-Suite™ directly from the infusion pump, clinicians can be assured of accurate fluid infusions. Medical errors related to incorrect data entry and incorrect calculations are reduced."

Systems like Guardrails™ and CareSuite™, while helpful in decreasing medication errors, all suffer from the same vulnerability, namely operator error. One such error arises, for example, when the wrong drug concentration, or even the wrong drug, is mixed by a hospital pharmacy. As the intravenous administration systems cannot identify the composition or concentration of an intravenous infusion, drug swap or admixture concentration errors are not prevented. U.S. Pat. No. 6,070,761 to Bloom et al attempts to deal with this problem during the vial loading process by standardizing and automating drug mixture and then verifying that the drug is the correct one for a given patient. Networking to one or more databases performs the verification. The system envisions various security and quality control features such as bar codes and passwords. Although this system may potentially lessen the likelihood of human errors, it cannot eliminate them, because it cannot positively identify the infusate.

Another unfortunate issue has been that of medical personnel deliberately administering unprescribed, dangerous, and even fatal types or doses of medication. One reported case resulted in the criminal conviction of a medical professional who administered muscle relaxants to ICU patients, resulting in a number of deaths. Currently, there is no system to automatically alert medical staff to this kind of danger. Errors of omission also occur in the administering of medications. As an example, such an error could occur when scheduled doses, whose timing is critical, are omitted or administered at unscheduled times. A system that automatically identifies the drug, time of administration, and dosing would serve as a quality control system to prevent inadvertent medication errors, as well as a deterrent to the deliberate misuse of the drugs or the omission of scheduled doses.

The pharmaceutical manufacturing industry, where real-time, on-line analysis of compounds is helpful for quality assurance and compliance with FDA GMP (Good Manufacturing Procedures) regulations, has automated systems that perform qualitative and quantitative analysis. These systems provide an automated analytical capability using spectroscopic analysis. A spectrometer passes a continuous portion of the electromagnetic spectrum through a specimen to develop an absorption spectrum. To establish a compound's identity, the absorption spectra can then be compared to spectral libraries of specific compounds. This identification process can be digitally automated. Quantitative analysis based on chemometric algorithms is then possible. The Beer-Lambert law, where all variables except concentration are known, can be used to perform the quantitative analysis. In present commercial applications, spectral databases use wavelengths in the range of 1–15 microns. The commercial devices, however are too large and too expensive for incorporation into clinical use.

Medical applications of spectroscopy are known. For example, Robinson, in U.S. Pat. No. 6,278,889, discloses a quantitative spectroscopic system to noninvasely determine in vivo glucose concentrations. Robinson also discloses the basics of quantitative spectroscopy. Unfortunately, Robinson's system is complex and costly due to 1) a variable path length and 2) a multiplicity of absorbing substances within the light path other than the analyte of interest.

U.S. Pat. No. 6,122,536 to Sun et al discloses an in vivo invasive infrared (IR) emitter and sensor for quantitative determinations of circulating analytes. The complexity of this system is due to the multiplicity of analytes and tissue components lying within a variable and, at times, a changing optical path length. The ideal situation for qualitative and quantitative spectroscopy exists when a single compound is suspended evenly in a relatively non-absorbing and spectrally known medium, and enclosed in a vessel relatively transparent to electromagnetic radiation and having a known spectral profile. Ideally, the vessel has a fixed, known optical path length. A fixed and known path length would, however, be unnecessary in systems utilizing Raman spectroscopy. Reflectance-based systems and qualitative systems without quantitative capability would also not require a fixed optical path length.

Rapid advancements in the areas of solid-state electronics, optoelectronics, and microprocessors have allowed the commercial production of high quality and inexpensive components in spectroscopic analysis. Various combinations of hardware and software can now perform rapid spectral data acquisition and analysis functions inexpensively. Medical and non-medical applications of these technologies are known. For example, pulse oximetry utilizes an LED-photodiode arrangement whereby two frequencies are sequentially passed through perfused tissue to determine oxygen saturation levels of hemoglobin. The transmittance ratios of these two wavelengths are then compared to an empirically derived and stored nomogram to determine the percentage of oxygen saturation. One example of such a device is U.S. Pat. No. 4,621,643 to New, Jr. et al.

The present wavelength range of commercial LED's is about 400–1,600 nanometers, or 0.4–1.6 microns. One example of an LED application, U.S. Pat. No. 5,995,858 to Kinast, discloses a phase-shifted, dual LED oximeter, which increases the signal to noise strength. The LED-photodiode probes used in the oximeter are the size of a band-aid and are inexpensive enough for a single, disposable use. Rosenthal, in U.S. Pat. No. 4,286,327, has devised an LED-based system for quantitative analysis of grain. McDonald, in U.S. Pat. No. 6,072,576, discloses an on-line, real-time Fourier Transformed near infrared (FTNIR) based system for process control in a chemical plant. Similarly, Ditmarsen, in U.S. Pat. No. 6,236,048, discloses a spectrally based system for characterization of a flowable material. Axon, in U.S. Pat. No. 6,362,891 discloses an FTNIR system for quality control of pharmaceutical tablet ingredients. It is noted that permissible tolerance levels of the ingredients are set for comparison to known levels, but thereafter unskilled operators are able to operate the system. Schnell, in U.S. Pat. No. 4,620,284, discloses a Raman-based system for qualitative and quantitative analysis using primarily a photodiode array for signal collection prior to comparison with known spectra.

To provide safer intravenous infusion would require that any qualitative or quantitative analysis of the infusate have some direct operative connection with the infusion process. Medications are often administered intravenously in a hospital setting utilizing a bag containing the added medication, an intravenous administration set, and an infusion pump. One conventional type of infusion pump system employs a peristaltic pump in conjunction with an intravenous administration set. The administration set consists of flexible thermoplastic tubing through which fluid flows from a suspended container, such as a flexible bag or rigid bottle, to a patient's vein. Much of the prior art relating to pumps is directed to delivering an accurate infusion rate, because an inaccurate infusion rate will lead to potentially dangerous incorrect doses of medications and fluids. One example of an infusion pump is U.S. Pat. No. 6,261,262 to Briggs et al. IV administration sets, such as U.S. Pat. No. 5,226,886 to Skakoon et al, provide tubing that carries the intravenous fluid through the infusion pump and to the patient.

Numerous models of IV infusion pumps and IV administration sets are commercially available. A typical system would be like that of the Horizon family of pumps and Horizon IV sets sold by B. Braun. All pumps in this family deliver infusions by positive pressure, which is generated through a volumetric displacement reservoir. This reservoir is incorporated within the IV administration set tubing, which is loaded into the pump via a door mechanism. The pump is set to run at a certain rate and activated. Alarms typically indicate some or all of the following problems: air-in-line, container empty, door open, downstream occlusion, hold time exceeded, low battery, low flow, system error, and upstream occlusion. Other common features include a dose/rate calculator mode, which automatically calculates the rate when dose information is entered, or the dose when rate information is entered. "Smart Pumps" can have preprogrammed institutional drug limits. The newest pump in the Horizon series, the Outlook™ incorporates bar code scanning technology to reduce drug administration errors. Even this technology, however, cannot account for errors such as incorrect admixture or incorrect labeling of the drug containers.

Ultimately, the existing safety systems related to intravenous infusion attempt to ensure that the right drug, in the right dose, is given to the right patient, with the right route of administration, at the right rate and strength, and at the right time. They all fail, however, because they lack a real-time ability to identify pharmaceutical or other compounds while these substances are being delivered to the patient. Such a system would further reduce medication errors. It would also permit data capture, storage, and analysis. Such a system could, for example, be integrated with a computer order entry system to form a complete feedback loop for quality assurance, maintenance of patient records, generation of bills, or even research and statistical analysis. It could, for example, eliminate the need for nurses to chart the administration of intravenous medications. At the present time, no mechanism exists that can perform these functions, because no automated mechanism exists for the qualitative and quantitative analysis of the drugs as they are intravenously provided to a patient.

SUMMARY OF THE INVENTION

The safety and efficiency of the administration of intravenous pharmaceuticals can be improved by adapting the infusion process for spectroscopic analysis. This approach is feasible and would solve many of the problems previously identified. The medications are individually mixed with carrier solutions that are weak absorbers in the ultraviolet (UV), visible (VIS), and near infrared (NIR) range. These solutions are administered with intravenous administration sets made from polyvinylchloride or other similar polymers, which are also weak absorbers in the UV-VIS-NIR region. Typical medication carriers, such as 5% dextrose in water or 0.9% sodium chloride solution, and the polymers within the intravenous (IV) administration sets, have known spectral profiles which can easily be compensated for in the qualitative and quantitative determinations of the compounds of interest.

The present invention qualitatively and quantitatively determines fluid path components in intravenous infusions for medical patients. In one preferred embodiment, it utilizes an IV administration set containing an optical window in conjunction with an IV infusion pump. Preferably, the pump contains embedded hardware and software to perform the spectral analysis of the fluid path components. By implementation of the present invention, errors of medication administration may be prevented. In addition, the invention may include warning mechanisms, fail-safe infusion shutoffs, means for automated recording of administered drugs, and other features facilitating administrative documentation and quality control.

In one embodiment of the invention, an infusion pump is used in the spectroscopic analysis of an intravenously delivered fluid. The analysis identifies one or more of the fluid's components, and preferably also determines their concentration. The pump includes a housing with an exterior and an interior. An intravenous administration set is used to deliver the fluid. The fluid follows a path through the interior of the pump housing. An emission source disposed within the housing directs a predetermined spectrum of electromagnetic radiation (EMR) at the fluid. A detector disposed within the housing detects that portion of the radiation transmitted, absorbed or reflected by the fluid, depending on the type of spectroscopic system. The detector produces an electronic signal used to spectroscopically analyze a component or components of the fluid. In the preferred embodiment of the invention, light-emitting diodes (LED's) are used for the emission source, and the exterior of the pump has controls and a display for controlling the spectroscopic analysis. In other embodiments of the invention, the control of the analysis and the display of its results can be performed remotely by various peripheral devices like keyboards and monitors.

In another embodiment of the invention, a process is used to more safely deliver intravenous fluid to a patient, thus reducing or even eliminating the medical errors previously discussed, such as wrong drug and wrong concentration errors. The process includes the steps of providing the fluid to be intravenously delivered and connecting it to an intravenous administration set. The intravenous administration set is connected to the patient, and the fluid is spectroscopically analyzed. Preferably the analysis is performed by providing an EMR emission source and detector on opposite sides of a fluid path, although other systems, such as Raman or reflectance, can be used. The detector generates a signal that is used to perform the spectroscopic analysis. In one preferred embodiment of the process, light-emitting diodes are used as the emission source. In another embodiment, the administration set is operatively connected to the infusion pump. An analysis of the detector signal can provide the identity and concentration of the medication. If the detector signal is coordinated with the rate information from the pump, then the dose can also be determined.

In yet another embodiment, the invention comprises a system that includes a spectroscopic analyzer separate from the infusion pump. In one embodiment, the analyzer can be a self-contained unit that fits around the tubing of the intravenous administration set. It can even be used with a gravity drip and no infusion pump. The analyzer has an EMR emission source and detector adjacent to the fluid path through the analyzer. Variations of this embodiment are also contemplated. For example, the analyzer can include all of the hardware and software necessary to perform the spectroscopic analysis. Alternatively, the ability to perform the analysis can be provided in a device located in the same room as the patient, or at a remote location such as a nurse's station. A keyboard and display can be included with the analyzer, or they can be peripherally attached in the patient's room, as with the peripheral attachments of desktop personal computers. In another variation, the analysis can be controlled only remotely, such as from the nurse's station, or both remotely and from in the patient's room. Here, too, the analyzer provides the identity and concentration of the medication. When combined with rate information from the pump, the delivered dosage can also be determined.

In still another embodiment, the invention comprises an intravenous administration set having tubing to supply intravenous fluid to a patient. The administration set includes an optical window that permits the transmission and detection of EMR for use in a spectroscopic analysis of the fluid's components. In the preferred version of this embodiment, the optical window is in an optical chamber that creates a more precise optical path length for the spectroscopic analysis.

As a result of the present invention, the medical field can now prevent wrong drug and wrong concentration errors. This ability can now be combined with existing or easily adaptable electronic devices and software to also minimize or eliminate errors relating to wrong dose, wrong concentration, wrong administration time, and even wrong patient. Even in the simplest of embodiments, the present invention will provide improved care and increased deterrence. Nurses and other medical personnel will be more attentive knowing that any incorrect drug or improper dose will be recorded, and it will be more likely that system errors can be identified. Additional features and advantages of the present invention will become apparent when considered in conjunction with the accompanying drawings and the detailed description below.

DETAILED DESCRIPTION OF THE PREFERRED EMBODIMENTS

Figure 1:
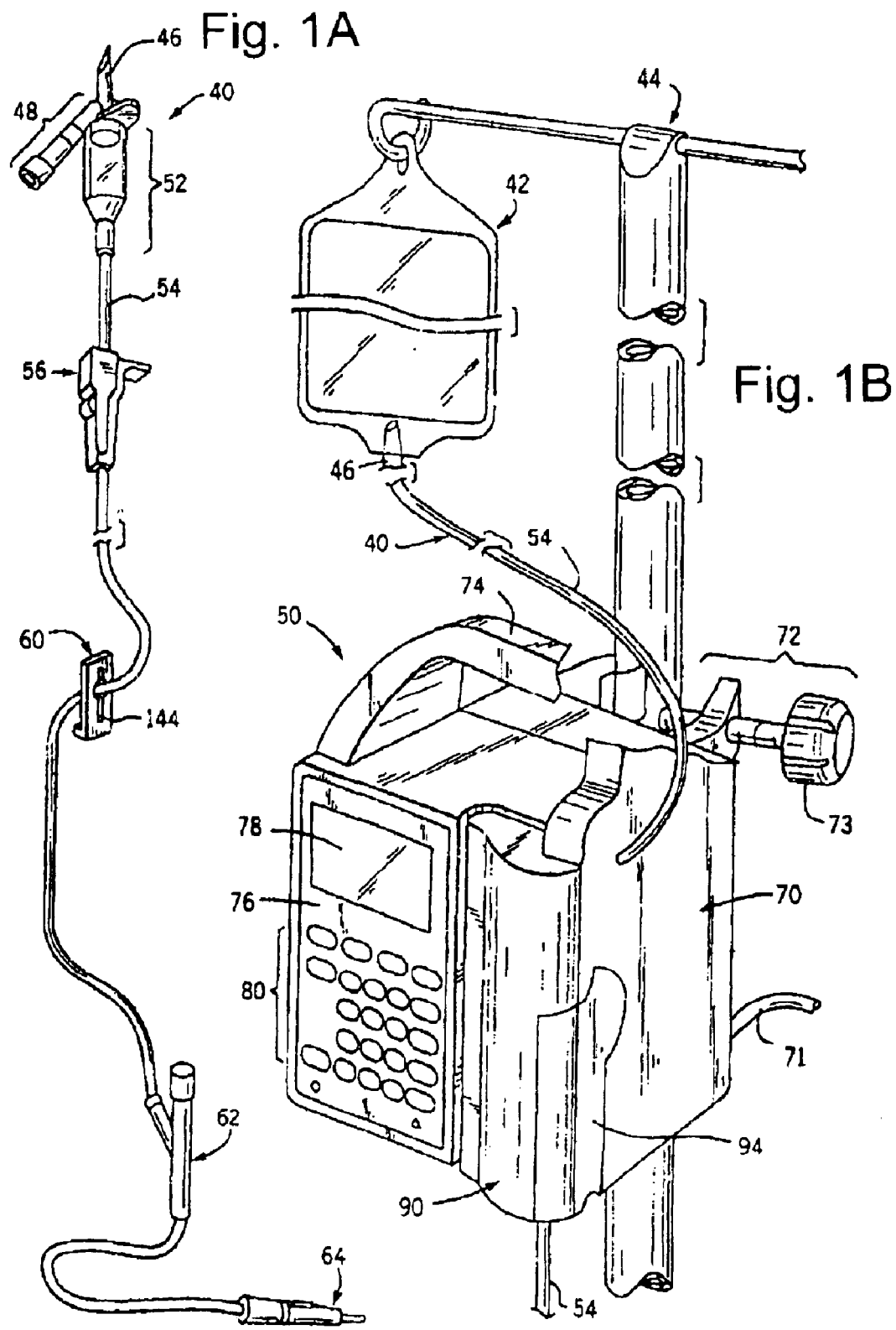
FIG. 1A is a perspective view of an intravenous administration set.
FIG. 1B is a perspective view of an infusion pump that is mounted on a stand and can be used with the administration set.

Two examples of the present invention are discussed below in connection with FIGS. 1–11. The first example uses a three LED array to check for the presence of morphine HCL. It is discussed with reference to FIGS. 1–7. Morphine is used as an example because the JCAHO has identified narcotics as one class of agents involved in a significant number of medication errors. The embodiment in FIGS. 1–7 might be used, for example, in Patient Controlled Analgesia (PCA) pumps. PCA pumps are dedicated for use typically with one of three narcotics: morphine, dilaudid, or demerol. An LED-based system for this application would be inexpensive and would be able to qualitatively and quantitatively function with a minimum of spectral data points. The second example, in FIGS. 8–11, utilizes a photodiode array collector and IR broadband emission source. This arrangement could be employed for a system that processes a large number of different pharmaceutical compounds. It could be updated by the inputting or downloading of reference spectral data to its memory.

FIG. 1A depicts a typical IV administration set 40. FIG. 1B depicts a typical peristaltic infusion pump 50 that measures the flow rate of intravenous fluids being delivered through administration set 40. The administration set 40 is typically employed to deliver parenteral fluids, medications, whole blood, red blood cell components, and the like from a fluid container, such as a bottle or flexible bag 42. Bag 42 is shown in FIG. 1B supported on an intravenous administration stand 44. A portion of the administration set 40 is engaged by the peristaltic pump 50, and a distal portion of the administration set 40 downstream of the pump 50 can be connected to a patient's indwelling vein access device, such as a needle or cannula (not illustrated), which is inserted into the patient.

The administration set 40 has a hollow piercing pin 46 projecting from a conventional bacterial filter 48 at the upper end of a drip chamber 52. A length of hollow flexible tubing 54 extends from the bottom of drip chamber 52 through a roller clamp 56. Disposed on tubing 54 downstream of the roller clamp 56 is a slide clamp 60. A conventional Y-injection site 62 is provided on the tubing 54 downstream of the slide clamp 60. The distal end of the tubing 54 is provided with a conventional male adaptor 64, which is designed to be attached to a venipuncture device (not shown). The IV administration set in FIG. 1A and adapted for use with the present invention is preferably constructed of a standard medical grade polymer such as polyvinylchloride (PVC), which has known and minimal absorption in the UV-VIS-NIR wavelengths.

Other typical IV administration sets are configured differently and may have more or fewer components. For the purpose of the present invention, the important aspect of the administration set is the tubing that carries the fluid through the infusion pump and to the patient. Thus, the use of the term IV administration set can also be understood broadly to be just the tubing. To the extent the present invention may require other features to operate, the administration set should be understood to include typical features of an administration set, such as drip chamber 52, roller clamp 56, adaptor 64, or a venipuncture device.

As shown in FIG. 1B, the pump 50 includes a housing 70 and a clamp 72 with knob 73 by which the pump 50 can be mounted to stand 44. A handle 74 projects upward from the top of the housing 70. The exterior of pump 50 has a front panel 76 containing a liquid crystal display 78 and a key pad 80. Next to front panel 76 is a front door 90 with handle 94. Tubing 54 passes into, through, and out of the interior of pump 50, where the flow rate of the intravenous fluid is physically controlled according to parameters entered on key pad 80.

Figure 2:
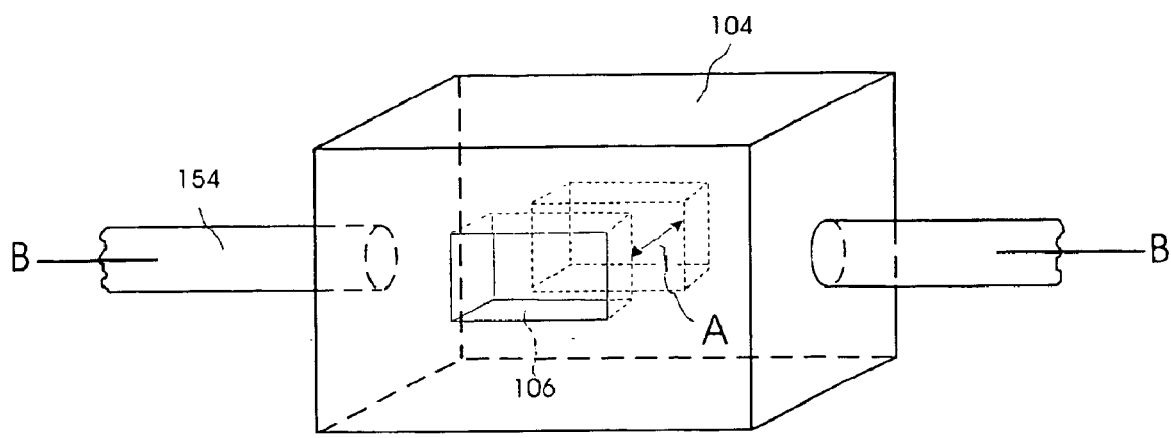
FIG. 2 depicts an optical chamber with recessed optical windows.

FIG. 2 shows tubing 154 passing through optical chamber 104. Preferably optical chamber 104 consists of a fixed dimension, parallel-walled structure configured to be included in an infusion pump housing. Optical windows 106 are physically recessed within optical chamber 104. This protects the optical windows 106 from damage or smudging, which in turn could distort EMR absorption and reflection values. IV tubing 154 and optical chamber 104 with fixed optical path length A would be primed with the infusate. A fixed length optical path would not be a requirement of a solely qualitative, transmission-based system or a system based on reflectance or Raman spectroscopy.

Figure 3:
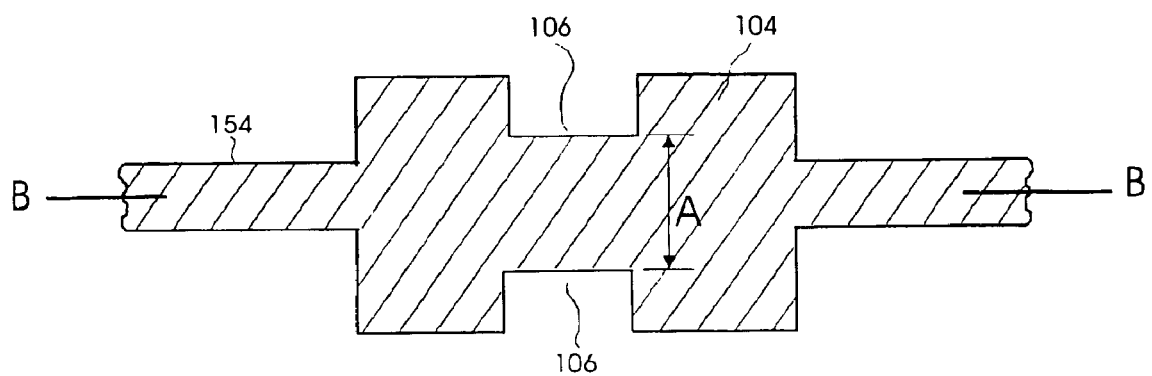
FIG. 3 is a plan view along section B—B of FIG. 2, depicting the recessed optical windows within the optical chamber.

FIG. 3 is a plan view through section B—B of FIG. 2 showing recessed optical windows 106 delineating path length A. As depicted in FIG. 3, the optical window 106 is that part of the optical chamber through which EMR traverses. It may or may not be recessed, may or may not be of the same composition as the optical chamber, and may be positioned on both sides of the optical chamber in transmission-based systems. It could, however, in the case of a reflectance or Raman system be a single window on one side of chamber 104. As discussed below with respect to other possible embodiments, the term optical window should, where appropriate, be interpreted in its broadest sense as permitting the passage of EMR. Alternatively, the one depicted in FIG. 3, it can have a discrete physical structure, such as the one depicted in FIG. 3.

Figure 4:
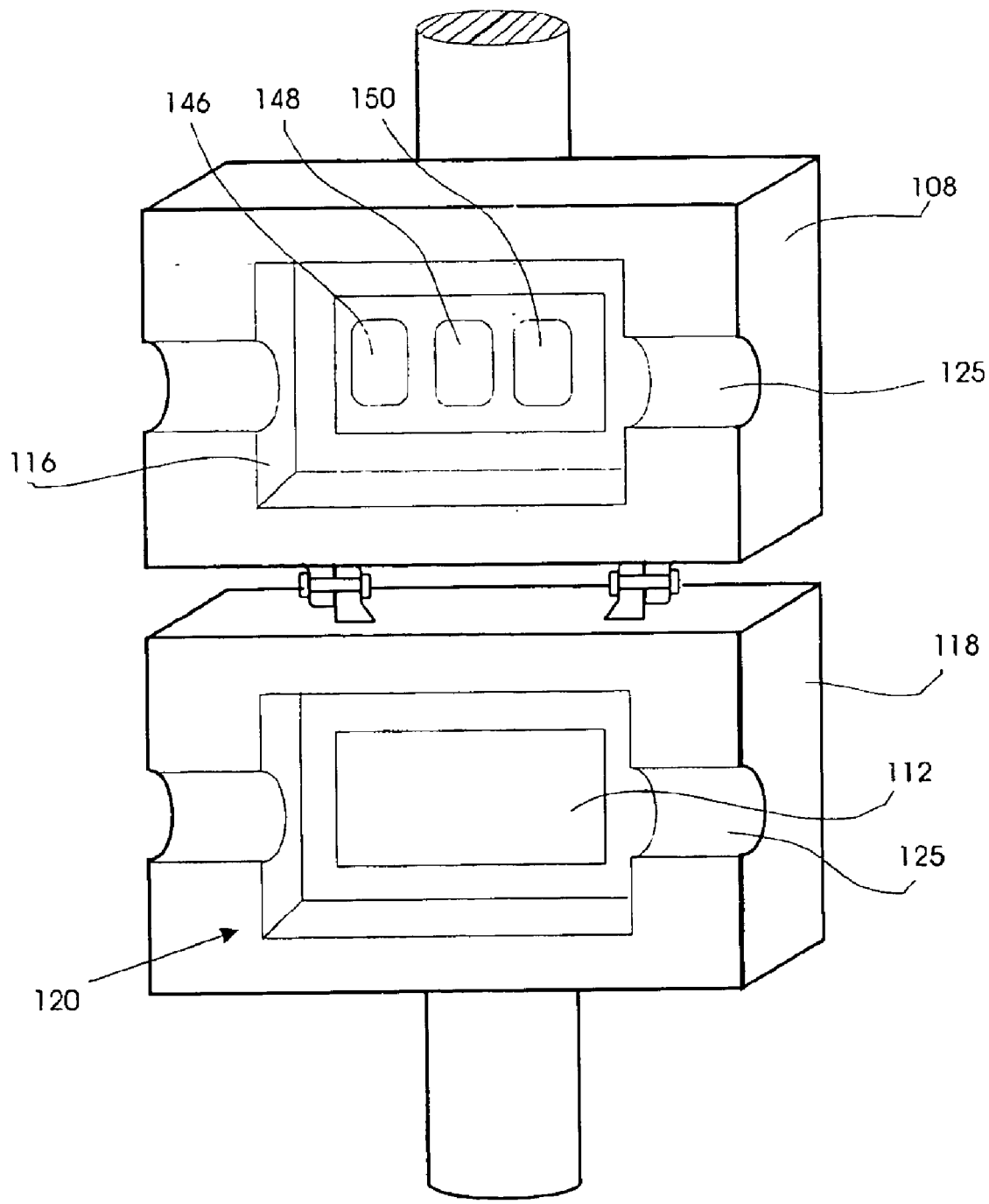
FIG. 4 schematically depicts a pole mounted pump housing with an LED array, photodetector, and an indentation to position the optical chamber.

FIG. 4 schematically depicts a hinged intravenous pump housing 108 in the open position. Only aspects of the present invention are shown and described. Other conventional aspects related to pump control, monitoring, warning and the like are not shown. An array of three LED's 146, 148, 150, and photodetector 112 are located in receptacle indentation 116, in the pump's interior 120. Notch 125 is adapted to hold tubing 154. Loading optical chamber 104 into infusion pump 108 and closing door 118 linearly aligns optical chamber 104 between LED array 110 and photodetector 112. Mirrors, choppers, fiberoptic bundles, and other optical devices (none of which are shown) can be utilized to deliver the EMR in various ways, such as a point source. In the preferred embodiment, tubing 154 includes optical chamber 104 that provides the fixed optical path required for quantitative analysis. It is also possible to eliminate optical chamber 104 and secure tubing 154 in a predetermined path in the pump's interior. Simply securing tubing 154 between LED's 146, 148, 150 and photodetector 112 may provide an optical window through the tubing with enough of a fixed optical path length without varying the cross-sectional configuration of the entire length of tubing. There is concern, however, that the flexibility and roundness of tubing 154 may vary the optical path length from one use to the next, depending on how the tubing is manually placed in the pump. That is why the preferred embodiment includes optical chamber 104. In FIG. 4, notch 125 and indentation 116 hold tubing 154 and optical chamber 104 securely within the pump interior 120. The tubing 154 and optical chamber 104 provide a path for the intravenous fluid that takes it between LED array 110 and photodetector 112 to enable the spectroscopic analysis. The term fluid path should be understood to encompass a meaning necessary to understand the claims and to enable the present invention. The path, for example, may simply be a portion of tubing or it may be a location inside the pump where the tubing is placed.

In one embodiment of the invention schematically depicted in FIG. 4, the exterior of pump housing 108 can include a key pad (not shown) and display (not shown) similar to key pad 80 and display 78 in FIG. 1B. The key pad can be used to preprogram numeric, alphanumeric, or even alphabetical information that identifies important parameters such as the identity of the fluid components to be analyzed, the maximum allowable concentrations of medication, information related to dose scheduling, and even administrative options such as patient name or number and whether the information should be saved or transferred to a remote database. In the preferred embodiment the fluid components are medications, or even components of the medications, that can be used to identify medication being administered to a patient.

Figure 5:
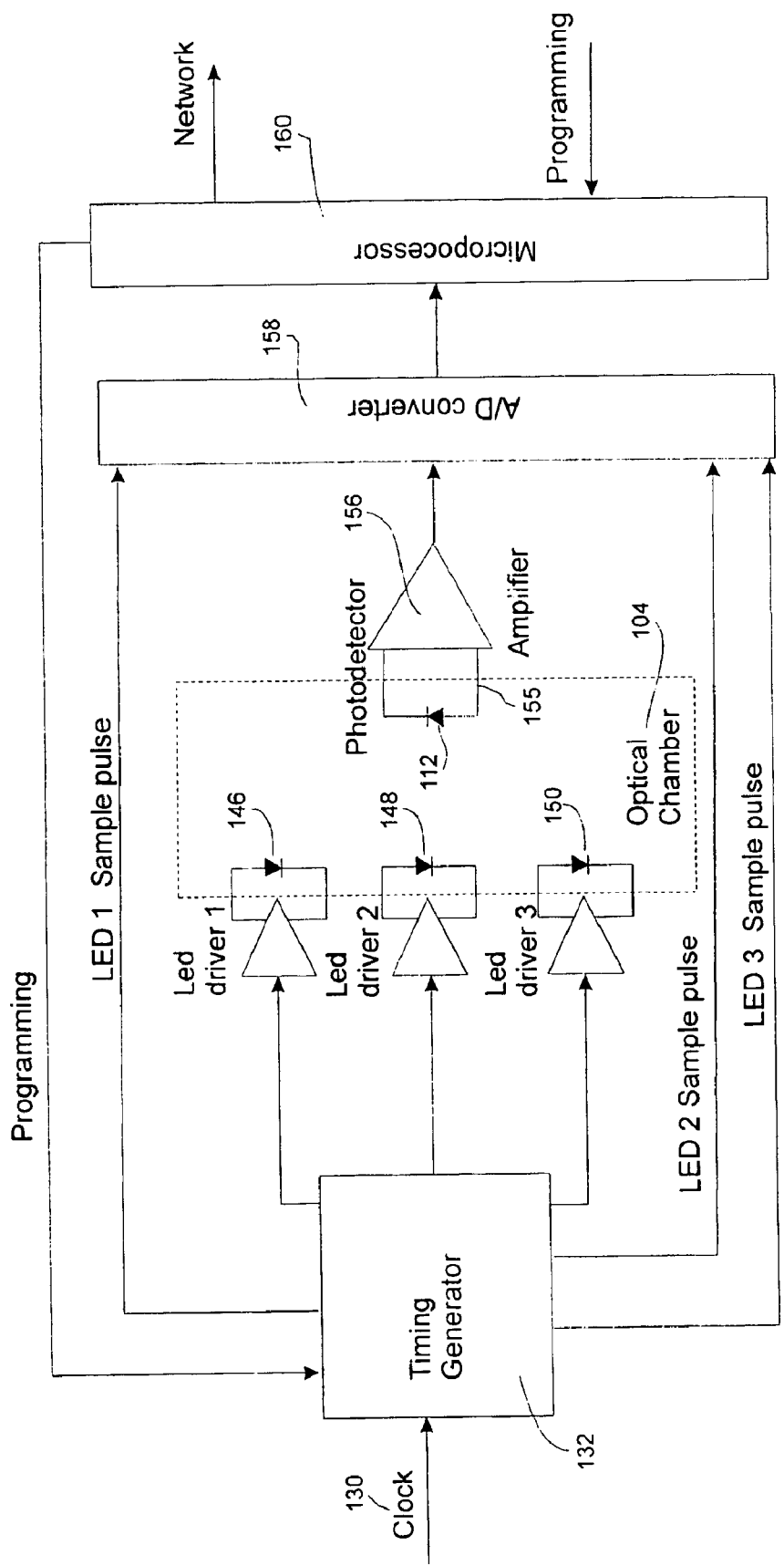
FIG. 5 is a block circuitry diagram of an LED array and photodetector schematically depicted in FIG. 4.

FIG. 5 is a diagram of the spectroscopic analysis. Clock 130 controls timing generator 132, which sequentially drives LED's 146, 148, 150. The optical output traverses the optical windows 106 (not shown) and optical chamber 104 and the infusate containing the compound of interest. The optical output is detected by photodetector 112. Photodetector 112 sends signal 155 to amplifier 156. The amplifier output is sampled by the A/D converter 158 as allowed for by LED timing sampling pulses 1, 2, and 3. The final output signal is sent to pre-programmed or programmable microprocessor 160, which can also control LED signal generation. Microprocessor 160 is preferably programmable and can provide network interfacing capability. Present LED wavelengths range from approximately 400 to 1600 nanometers. It is understood that longer wavelengths are under development.

Figure 6:
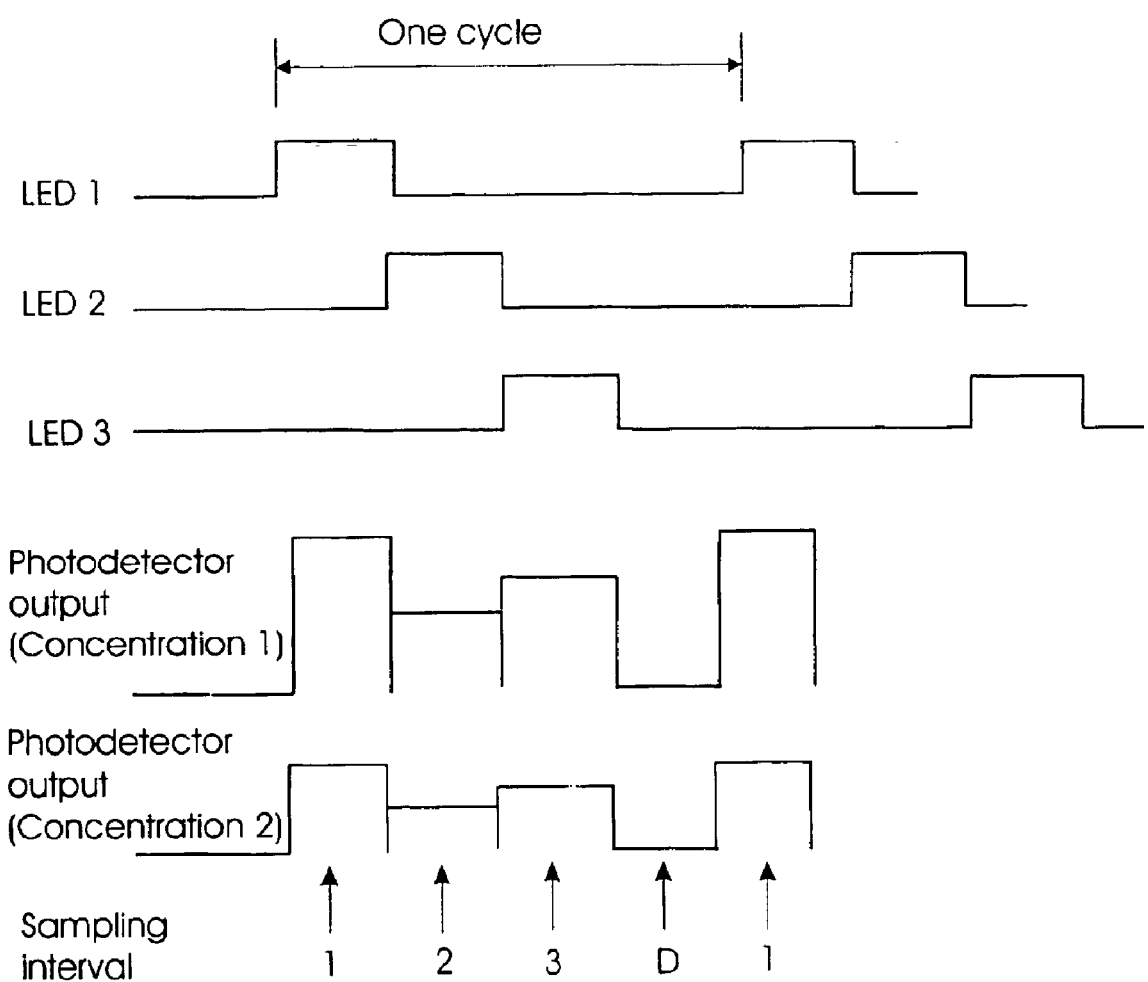
FIG. 6 is a timing diagram for a spectroscopic analysis using three LED's and depicts sampling intervals and output concentrations.

FIG. 6 shows a timing diagram in which the three LED's are sequentially driven, with one dark sampling interval. The dark period allows the continuous subtraction of ambient stray light from the LED transmissive values. One cycle is shown, with typical drive frequencies on the order of 300 Hz. The photodetector signal strength outputs are shown as a bar graph. This ratio of photodetector output is unique to and constitutes the unique identifier for any single pharmaceutical. The number of wavelengths necessary for the analysis may vary, depending on the number of pharmaceuticals in the universe and their underlying spectra. Though absolute signal strength varies, the ratio of signal strengths at the given wavelengths are concentration independent and constitute the unique characteristic of a particular compound, regardless of concentration. This ratio of signal strength is used to identify the compound by virtue of a comparison to known stored values. Photodetector outputs for single and double strengths of the same pharmaceutical compound are shown in FIG. 6 to illustrate this point: The output from the double strength solution of concentration 2 is Half that of concentration 1, but the transmittance ratios remain the same.

Figure 7:
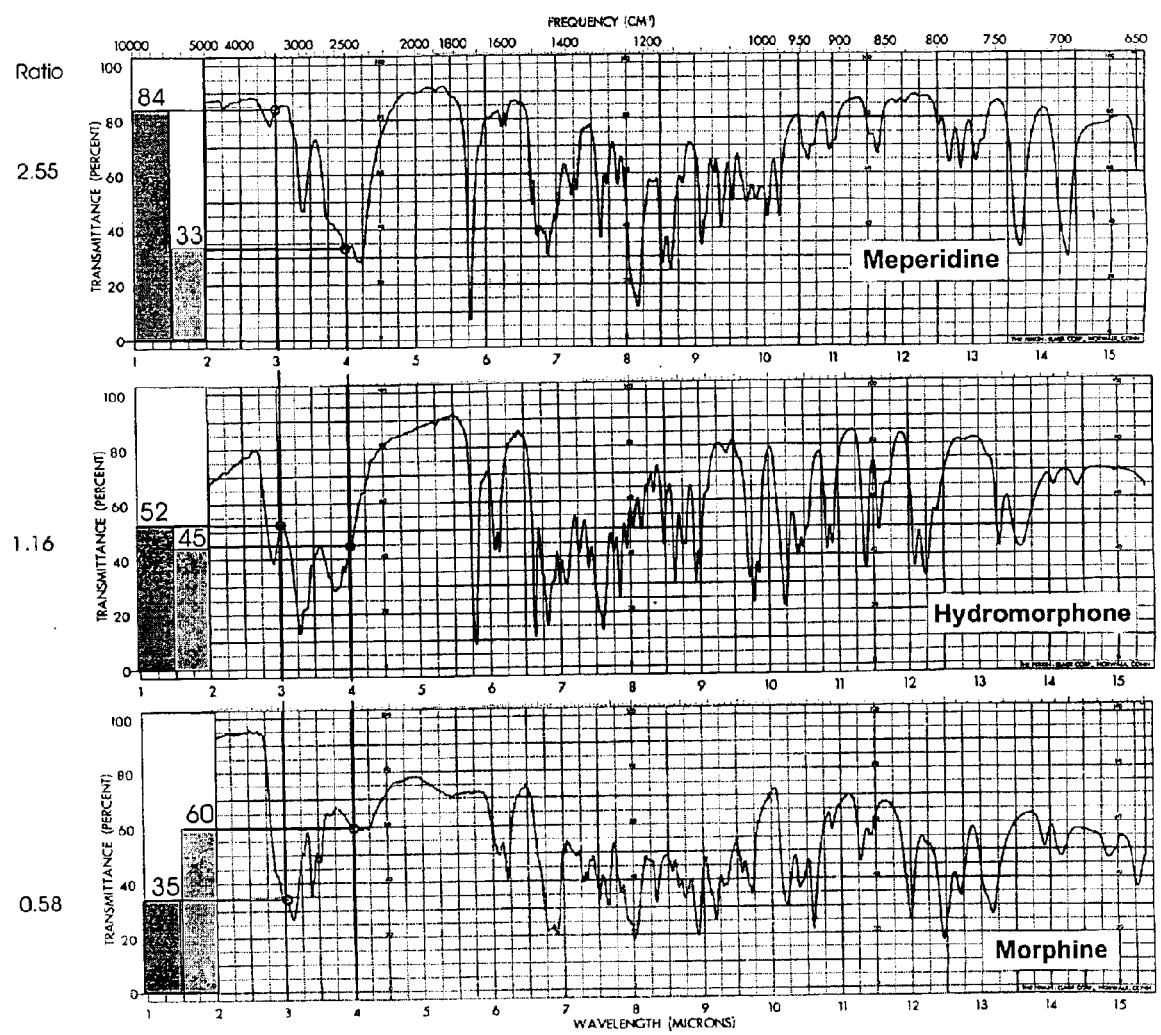
FIG. 7 shows the IR spectra of morphine, dilaudid, and demerol.

FIG. 7 shows the IR spectrum of morphine, hydromorphone, and meperidine. One can see that as few as two wavelengths are needed to generate a unique identifying ratio that enables differentiation in this limited drug universe. For example, percent transmittance corresponding to the 3 and 4 micron wavelengths are shown at the left in a bar graph format. Dividing the percent transmission at 3 microns by that at 4 microns results in the unique identifying ratios in the left-hand margin. It is appreciated that these ratios are concentration independent. Hence in some instances, a two-wavelength photodetector arrangement could be utilized with minimal cost.

A Patient Controlled Analgesia (PCA) pump provides a basic example. A hospital wants a qualitative confirmation (yes or no) and quantitative information (dose or concentration) concerning a drug universe of morphine, dilaudid, and demerol, for which it utilizes a dedicated PCA pump. In the present example, the nurse may input the drug, concentration, and patient identifier information. The pump would have its own microprocessor-based control and data handling functions for rate control and spectroscopic analysis. A keypad and display panel on the outside of the pump could be used to perform data input. Alternatively, one could use a separate monitor and keyboard, as with personal computers. The control and analysis functions could be provided through a network to the pump, in a patient's room, a nurse's station, or elsewhere. The drug container could be bar coded and scanned by the pump for comparison to computer-entered orders for the patient. Once the pump is programmed, the infusion is begun.

The pump can be programmed at the factory or at the hospital, or portions of the programming could be performed at each location. The type of programming would be determined by the number of specific pharmaceuticals and quantitative and qualitative data required. The choice of various hardware and software aspects of the programming and control of the pump are left to the designer. The pump would have a number of LED's as the emission source, some or all of which would be activated based on the unique identifier characteristic of the narcotics in the hospital formulary. These LED's and their respective outputs would then be activated in a timed manner such that the photodetector output ratios are concentration independent and able to qualitatively differentiate the compounds.

As an example, a three LED system might have four discrete sampling intervals for calculation purposes. In the first interval, the first LED would be energized and the emission would pass through the sample and be detected by the photodetector. The next interval would contain the photodetector signal from the second LED, and the third interval would contain the photodetector signal from LED 3. Interval four would sample signal generation due to ambient light without LED activation, which would be subtracted from all LED signals prior to calculation of the relative transmissive values.

The transmission ratio generated by the three LED array would then be calculated and compared by algorithm to known transmission values. The identification could be performed as a YES or NO query. YES causes the software to proceed to the quantitative aspect of the algorithm, if desired. NO leads to one of several actions depending on the programming. Most likely the programming will cause the infusion to stop and will give a readout of the error involved.

The calculation of the transmissive ratios, which are concentration independent because they reflect the relative signal strength output at specific wavelengths, allows the system flexibility to deal with the absorptivity of varied concentrations. Concentrations will vary with dosage, admixture techniques, etc. Transmissive ratios will, however, remain constant regardless of concentration and will function as the unique identifier for any given compound.

The quantitative analysis begins by selecting at least one wavelength which has a known percent transmission greater than 0 and less than 100 percent. If all other variables except concentration are known, the Beer-Lambert equation can solve for concentration. At a fraction of 300 Hz, the concentration is determined, multiplied by the infusion rate, and then integrated over time to tabulate the total dosage. For safety, it is preferable that the step of qualitative confirmation always be performed before any quantitative analysis. Otherwise, programming only for a quantitative analysis of the drug risks propagating a wrong drug error. The hardware and software components for using the spectroscopic data will vary according to the user's requirements. Different healthcare facilities have different clinical and administrative needs. Simpler requirements may include qualitative identification and/or quantitative data for a single agent. More sophisticated requirements could necessitate both qualitative and quantitative analysis for a complete and ever expanding pharmacopoeia.

In the situation where a hospital desires an expanded ability to qualitatively and/or quantitatively determine fluid path constituents, a system utilizing a photodiode array detector could be employed. This system would likely cost more than a basic LED system but would have the advantage of generating a vast number of spectral data points quickly and accurately. Many types of equipment could be employed, including different emission sources, such as a tungsten, halogen, or incandescent lamp for generating a broad spectrum of wavelengths. A variety of detectors could also be used, such as photovoltaic and photoconductive cells, vacuum phototubes, photomultipliers, photodiodes, and charge coupled devices. The examples of an LED and PDA-based system are given as preferred examples of an inexpensive system, but they are not intended to limit the scope of the invention. Various embodiments of the invention with any given emission source would function well with an appropriately matching detector.

Figure 8:
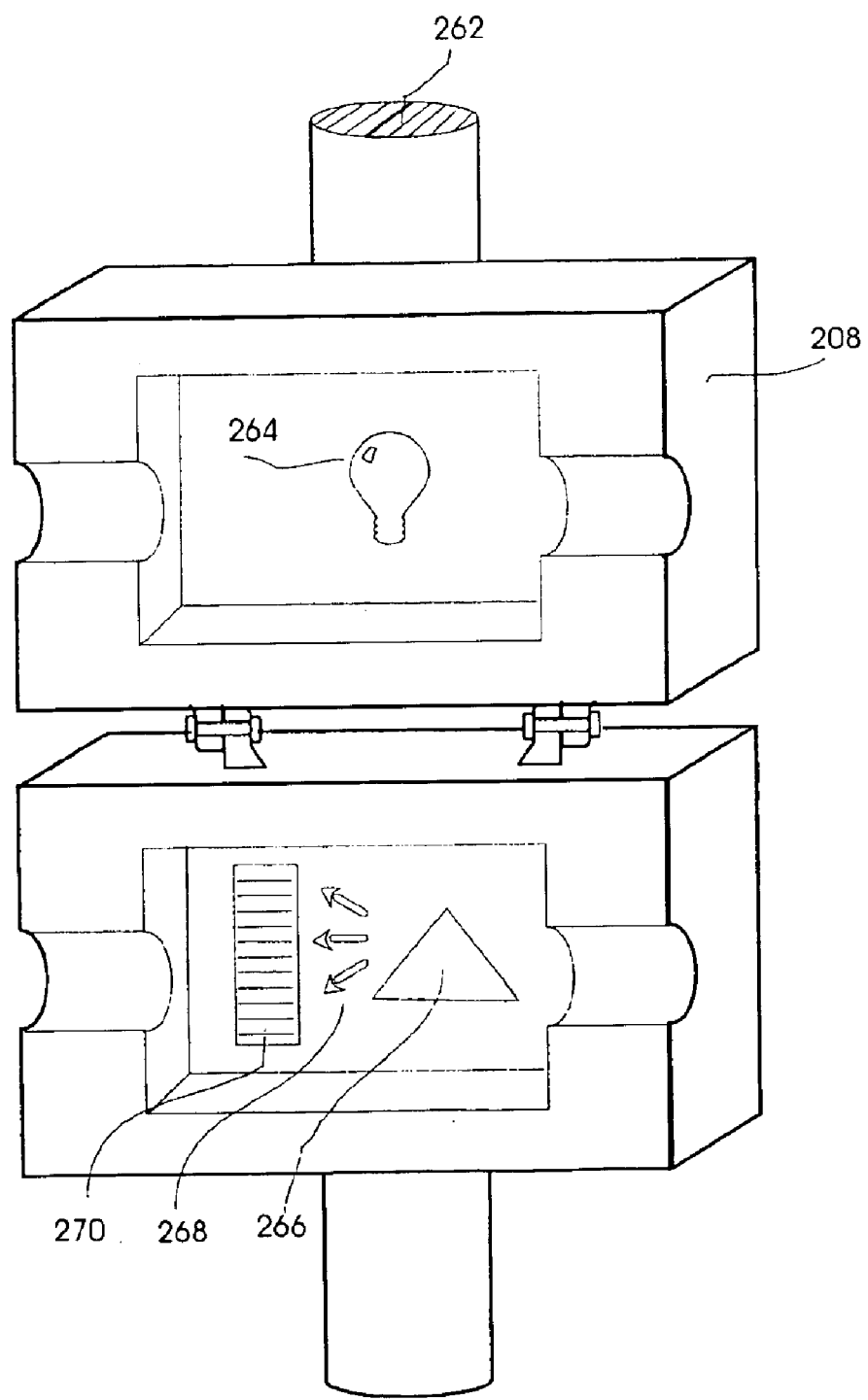
FIG. 8 schematically depicts a pole-mounted IV pump housing with an infrared emission source and a photodiode array detector.

FIG. 8 depicts an alternative embodiment where the emission source is a broadband infrared emitter and the data generated is absorbance. The emission source could use various EMR wavelengths, depending on the underlying spectra of the pharmaceutical universe. Likewise, reflectance, Raman, or any other spectral data could be gathered and analyzed. IV pump housing 208 is mounted on pole 262 and is again schematically depicted without details relating to infusion rate components. Emission source 264 in this embodiment emits over the range of 1–15 microns, which is the typical range of existing commercial spectral databases. This range allows "fingerprinting" of compounds, i.e., the determination of fluid components independent of their concentration. This data is digitally compared to stored reference data at predetermined confidence levels. Many mathematical algorithms are capable of analyzing the data.

The emission from source 264 traverses the optical window and optical chamber containing the IV infusate (not shown) and is diffracted by prism 266 or a holographic grating (not shown). Diffracted radiation 268 is detected by photodiode array 270 and generates a multiplicity of signals. A CPU (not shown) controls the process, is programmable, and can acquire an entire spectrum in a fraction of a second. As before, the relative ratios acquired are the basis for a concentration independent identification of the compound when compared to stored spectral data. This process is repeated rapidly and the results averaged on an ongoing basis. Quantitative analysis can also be performed using chemometric analysis where the path length of the optical chamber is known and is integrated over time with the flow rate from the pump to result in a summation of dose delivered over time.

Figure 9:
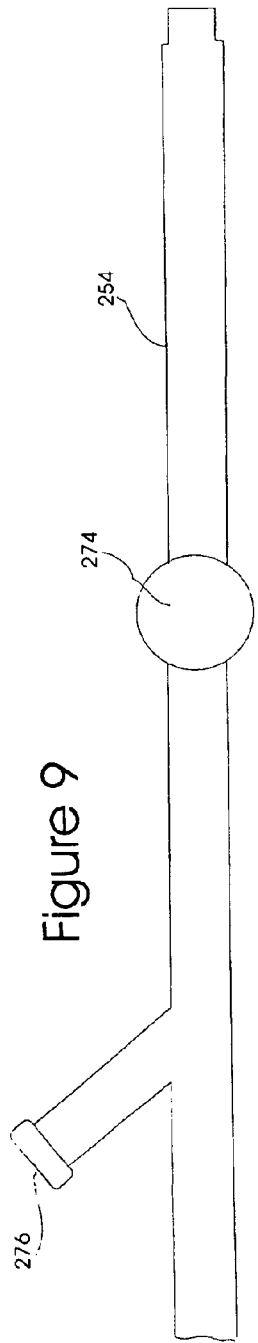
FIG. 9 depicts a portion of an IV administration set with an optical window.
Figure 10:
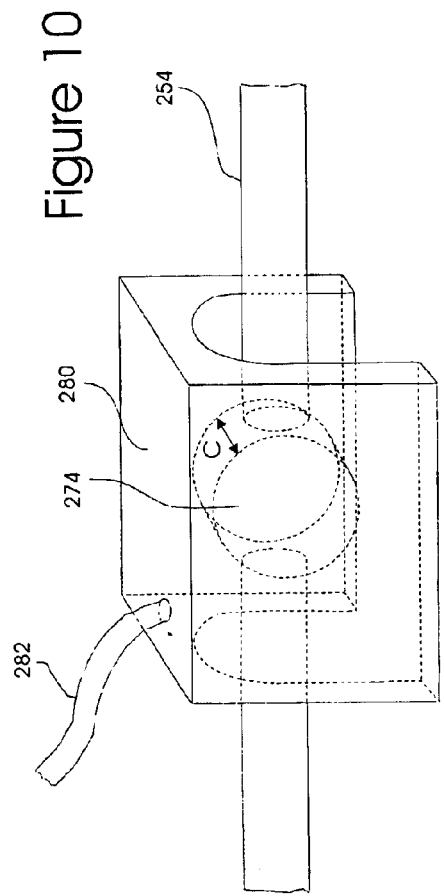
FIG. 10 depicts an optical housing covering the optical window.
Figure 11:
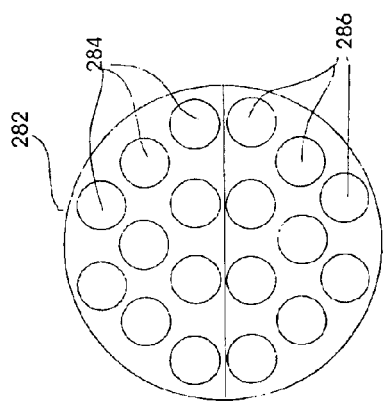
FIG. 11 is a cross section of a two-way fiberoptic bundle.

FIG. 9 shows a portion of an intravenous administration set with tubing 254, an optical chamber 274, and infusion port 276. In FIG. 10, optical housing 280 engages and covers optical chamber 274. Optical path length C is fixed between opposing walls of optical chamber 274. The walls of chamber 274 could be the optical windows through which the EMR passes. This arrangement would be used in situations such as the operating room, where IV medications are delivered by IV bolus. Here it would be advantageous to physically distance the emission source and detector hardware from the optical housing 280 by means of fiber optic cable 282. In FIG. 11, fiberoptic cable 282 is shown in cross section. Fiberoptic bundles 284 transmit the emission electromagnetic radiation to housing 280, and fiberoptic bundles 286 transmit the collected electromagnetic radiation to the detector hardware and software.

The preceding discussion of the present invention covers its basic structure and process. Those of skill in the art will realize that changes can be made in the fabrication and configuration of the invention, and that such changes can be made without departing from the spirit of the disclosed embodiments. For example, the description of the invention contemplates that an emission source and a detector will be permanently mounted in the pump housing, and that the spectroscopic analysis of the signals generated by the detector can be performed by the pump. This is accomplished by electronic hardware and/or software known or easily developed by those in the art. The information could be displayed by the pump, or it could be transmitted to and displayed at a remote location such as a nurse's station, or displayed at both locations. Similarly, the controls for the spectroscopic analysis could be pump mounted, remotely located, or both. The analysis can be performed by any combination of hardware and/or software. For example, pumps could use modules with different hardwired or programmable chips that could be swapped in and out of different pumps. Each chip would represent the analytical capability for one or more fluid components. Indeed, the emission source and detector could be configured to employ a Raman-based system for qualitative and quantitative analysis or a reflective-based system for qualitative analysis. While one preferred embodiment uses inexpensive LED's in a system based on transmission-absorption, the invention should not be so limited.

Other embodiments would have practical application. For example, a simple spectroscopic analyzer with an emission source and detector could be located in a structure remote from the pump. Such a device would be useful in the operating room, where drugs are given by IV push and only a qualitative analysis may be of interest. The term remote should be understood to mean that two structures are physically distinct. In terms of actual distance, they could be touching or they could be miles apart. Some examples will clarify this point. The emission source and detector could be located in a device adapted only for the spectroscopic analysis, and not for the rate monitoring function performed by the pump. Such a spectroscopic analyzer could be a separate housing clamped around the tubing of the IV administration set downstream from the infusion pump. An example would be somewhat like FIG. 4 (or FIG. 8), except that the structure depicted in FIG. 4 would be just the spectroscopic analyzer, and it would not have any infusion pump components or functions as described earlier but not show in the drawings. The analyzer could be mounted on the same stand as the pump or on a different stand, or, if light enough, simply clamped around the tubing with the intravenous fluid. It could be connected to the pump, where control and display of the spectroscopic analysis would still occur, or it could have its own control and display mechanisms. To quantitatively analyze the infusate, however, the analysis would require the infusion rate established by the pump. Some data link between the pump and the analyzer would be required. Like the embodiment in which the emission source and detector are mounted inside the pump, the electronic devices necessary to control and perform the spectroscopic analysis in a device separate from the infusion pump can be configured in a variety of ways. The analysis can be controlled and performed in the same device containing the emission source and detector, or various aspects of the control of the analysis and the analysis itself can be located remotely. The location and/or duplication of devices for control and data manipulation, such as keyboards, display panels, and hardware and software for spectroscopic analysis, are all a matter of choice. That choice is dictated by the needs of the medical services provider and the cost of any desired configuration. These choices do, however, permit the medical field to improve its ability to address all types of the medication errors that are discussed above.

Another example of variations to the invention can be seen in the tubing 154 and optical chamber 104. As noted earlier, one embodiment of the invention contemplates using just the tubing 154 with its cross-section determining the optical path length. Should one use the preferred embodiment in FIGS. 2 and 3, which include both tubing 154 and chamber 104, a variety of configurations are still possible. Chamber 104 need not be rectilinear in shape and need not have recessed windows 106. The primary consideration is maintaining optical path length A as fixed as possible in relation to the emission source and detector. Similarly, it is a matter of choice whether to fabricate chamber 104 and tubing 154 as a unitary structure from the same material. One possible embodiment could include an administration set that comes with two separate pieces of tubing that can be fixed to the optical chamber by medical personnel in a clinical setting. The chamber, in turn, can be placed inside the infusion pump by the medical personnel; it can be permanently constructed into the interior of the pump; or, it can remain outside the pump as part of a separate system for analyzing the fluid. Therefore, the term fluid path should be understood in its broadest sense to include those features necessary to give the term meaning. The fluid path may include a physical structure (or portion of it) containing the fluid or the tubing, it may represent a volume of space through which the fluid moves, or it may include something in between.

For simplicity, the invention has been described in terms a single fluid component. If more than one medication were provided intravenously to a patient, analysis of each medication would require a separate IV administration set with its own emission source and detector. This would be the case, for example, in intensive care units, where it is not unusual to provide a patient with four to six different medications, each associated with a separate infusion pump. It is, however, possible to develop a spectral database for a fluid with multiple components. A single emission source and detector could then be configured to provide the necessary wavelengths to simultaneously identify and quantify more than one pharmaceutical compound or fluid component being delivered through the IV administration set. In such a case, only one pump with one set of spectroscopic hardware and software would be necessary.

In yet other embodiments, the present invention could be adapted to functions other than the intravenous delivery of medication. One such function could involve kidney dialysis or similar procedures.

Therefore, in the spirit of the broad description of the invention, the invention is defined in the following claims.

What is claimed:

1. An infusion pump system for delivering an intended intravenous fluid to a patient comprising:
   a pump housing with an exterior and an interior;
   means for inputting the identification of at least one component of interest in an intended intravenous fluid;
   a memory device for storing at least one parametric value uniquely associated with said at least one component of interest,
   a fluid path disposed within the interior of the housing for conducting the intravenous fluid to be delivered;
   a first emission source positioned adjacent to the fluid path for directing electromagnetic radiation into the fluid to enable the electromagnetic radiation to interact with at least one component of interest;
   a first detector positioned adjacent to the fluid path for detecting the electromagnetic radiation emerging from the fluid therein and for generating a signal for use in spectroscopically analyzing at least one component of the fluid in the fluid path, and
   means responsive to said signal for permitting said infusion only if said signal is substantially indicative of an intravenous fluid in the fluid path having said at least one component of interest.

2. The pump system of claim 1, further comprising at least one of electronic hardware and software adapted to process the detector signal to spectroscopically analyze the at least one component of the fluid.

3. The pump system of claim 1, further comprising an optical chamber disposed adjacent the emission source and the detector and through which the fluid passes during spectroscopic analysis.

4. The pump system of claim 3, wherein the optical chamber is disposed between the emission source and the detector.

5. The pump system of claim 2, wherein said inputting means includes controls disposed on the exterior of the pump housing for controlling at least one parameter related to the spectroscopic analysis.

6. The pump system of claim 5, further comprising a display disposed on the exterior of the pump housing for displaying the at least one parameter.

7. The pump system of claim 6, wherein one parameter is representative of the identity of the at least one component of the fluid.

8. The pump system of claim 7, wherein the emission source comprises at least two light-emitting diodes.

9. The pump system of claim 8, wherein a second parameter is representative of a maximum dosage of the at least one component of the fluid.

10. The pump system of claim 9, further comprising a connection means to at least one of remote electronic hardware and remote software adapted to spectroscopically analyze the at least one component of the fluid.

11. The pump system of claim 1 wherein the detector includes means for detecting a spectral characteristic of fluid within the fluid path at at least two substantially non-overlapping electromagnetic radiation frequency ranges, and for producing a signal indicative of the detected spectral characteristic associated with at least two of said ranges.

12. The pump system of claim 11 including means for determining the ratio of the characteristic-indicative signals obtained for two substantially non-overlapping frequency ranges.

13. The pump system of claim 11 wherein the frequency ranges are respectively the frequency ranges within which the component of interest in the intended fluid produces a substantially minimum and substantially maximum signal level relative to all other frequency ranges.

14. The pump system of claim 1 wherein the inputting means is selected from the group consisting of at least one of (a) barcode reader means for scanning the barcode on a container of intravenous solution to transfer data indicative of the label-stated content of the container, (b) keypad entry means for entering data indicative of the desired content of the container, and (c) barcode reader means for scanning the barcode on a container of intravenous solution to transfer data indicative of the label-stated content of the container and keypad entry means for entering data indicative of the desired content of the container.

15. The pump system of claim 14 wherein the signal responsive means is responsive to the data supplied by the inputting means to permit infusion only if the inputted data and the spectral analysis of the fluid in the fluid path are all in accord.

16. The pump system of claim 1 including means for determining the concentration of the component of interest in the fluid contained in the fluid path.

17. The pump system of claim 16 including
means for inputting a parameter indicative of the desired concentration of the component of interest,
a second emission source for directing electromagnetic radiation at the fluid within the fluid path, and
a second detector for detecting the electromagnetic radiation emerging from the fluid in the fluid path, and
means for permitting delivery of fluid having said component of interest to the patient only if the level of detected radiation is substantially equivalent to the level that would be detected from the desired concentration of the component of interest.

18. The pump system of claim 17 including memory means for storing digital values pertaining to the levels of detected radiation that are expected from fluids of respective concentrations of the component of interest, and
memory access means responsive to the parameter inputting means to provide the delivery-permitting means with the value of said desired concentration.

19. The pump system of claim 16 including
means for inputting a parameter indicative of the desired concentration of the component of interest,
a second emission source for directing electromagnetic radiation at the fluid within the fluid path, and
a second detector for detecting the electromagnetic radiation emerging from the fluid in the fluid path,
integration means responsive to the infusion rate of the pump and the duration of the infusion to indicate the dosage of the component of interest infused into the patient,
means for inputting the desired dosage of the component of interest, and
means responsive to the integration means and the inputting means for permitting delivery of the fluid to the patient so long as the desired dosage of the component of interest has not been exceeded.

20. The pump system of claim 17 wherein said first emission source is capable of emitting electromagnetic radiation over a first range of frequencies, and
wherein said first emission source functions as said second emission source by emitting electromagnetic radiation within a second frequency range that is substantially non-overlapping with said first frequency range.

21. The pump system of claim 20 wherein the first detector is capable of detecting electromagnetic radiation within said first range of frequencies, and
wherein said first detector functions as said second detector by detecting electromagnetic radiation within said second frequency range.

22. The pump system of claim 1 wherein the detector is disposed within the housing interior.

23. The pump system of claim 22 wherein the emission source is disposed within the housing interior.

24. The pump system of claim 1 wherein the emission source is disposed within the housing interior.

25. The pump system of claim 1, further comprising a cassette-like case defining an optical chamber through which the fluid passes during spectroscopic analysis, said case being disposed adjacent the emission source and the detector and having at least one optical window through which the fluid therein is optically coupled to the emission source and detector.

26. The pump system of claim 25 wherein the optical chamber defines a fixed length optical path between the emission source and detector.

27. The pump system of claim 3 wherein the optical chamber is defined within a cassette-like case sized to fit within the interior of the pump housing.

28. The pump system of claim 27 wherein the cassette-like case includes at least one optical window through which the emission source and detector are optically coupled to the fluid.

29. The pump system of claim 27 wherein the case includes a pair of opposing walls, with at least one optical window being recessed into at least one of the walls.

30. The pump system of claim 27 wherein the optical chamber is defined between at least two parallel case walls, and includes an optical window in each wall through which a respective one of the emission source and detector are optically coupled to the fluid.

31. The pump system of claim 27 wherein the pump housing includes a hinged door through which access to the cassette-like case is provided from the exterior of the housing.

32. The pump system of claim 31 wherein the hinged door includes means for substantially optically aligning the optical chamber with the emission source and detector when the door is closed.

33. The pump system of claim 27 wherein the cassette-like case includes means for securing a fluid-conducting tube in substantial optical alignment with the emission source and detector, and
means for fluidically coupling said tube to a source of intravenous fluid.

34. A process for reducing the risk of erroneously provided intravenous fluid delivered to a patient, comprising the steps of:
providing an intended intravenous fluid to a pump for intravenous delivery to a patient;
inputting the identification of at least one component of interest in the intended intravenous fluid to an intravenous pump controller;
positioning an administration set for fluidic communication with the intended intravenous fluid;
connecting the administration set to the patient to provide the fluid intravenously to the patient;
spectroscopically analyzing the fluid as the fluid is delivered to the patient to test for the presence of at least one component of the fluid and
permitting delivery to the patient only if the spectroscopic analysis is substantially indicative of an intravenous fluid in the fluid path having said at least one component of interest.

35. The process of claim 34, wherein the step of spectroscopic analysis includes providing an emission source and a detector adjacent to the administration set to generate an electronic signal for use in the spectroscopic analysis.

36. The process of claim 35 wherein the analysis uses a reflectance-based method of signal analysis.

37. The process of claim 35 wherein the spectroscopic analysis uses a Raman method of signal analysis.

38. The process of claim 34, wherein in the step of spectroscopic analysis is performed inside the pump housing.

39. The process of claim 35, wherein the emission source comprises at least two light-emitting diodes.

40. The process of claim 35, wherein the analysis of the electronic signal is performed at a location remote from the pump.

41. The process of claim 35, wherein the step of spectroscopic analysis includes providing an emission source and a detector adapted to analyze two or more components of the fluid.

42. The process of claim 41, wherein the emission source is a broadband emitter.

43. The process of claim 42, wherein the detector is a broadband detector.

44. A system for spectroscopically analyzing the components of an intravenous fluid to be delivered to a patient, comprising:

an intravenous administration set for delivering the fluid, the administration set having an optical window;

a spectroscopic analyzer operatively connected to the administration set, the analyzer including an emission source for directing electromagnetic radiation through the optical window at the fluid and a detector for detecting the electromagnetic radiation emerging from the fluid.

45. The system of claim 44, wherein the administration set passes between the emission source and the detector.

46. The system of claim 45, wherein the emission source comprises at least two light-emitting diodes.

47. The system of claim 45 further comprising at least one of electronic hardware and software associated with the spectroscopic analyzer.

48. The system of claim 47, wherein the at least one of electronic hardware and software is remote from the spectroscopic analyzer.

49. In an intravenous administration set having tubing to supply intravenous fluid to a patient, the improvement comprising:

an optical window adapted to permit the transmittance and detection of electromagnetic radiation for use in a spectroscopic analysis of the fluid.

50. The improved intravenous administration set of claim 49, further comprising an optical chamber containing the optical window.

* * * * *